(12) United States Patent
Weston

(10) Patent No.: US 9,339,600 B2
(45) Date of Patent: May 17, 2016

(54) SAFETY NEEDLE

(75) Inventor: Terence Edward Weston, Swannington (GB)

(73) Assignee: Salvus Technology Limited, Stradbroke, Suffolk (GB)

(*) Notice: Subject to any disclaimer, the term of this patent is extended or adjusted under 35 U.S.C. 154(b) by 774 days.

(21) Appl. No.: 12/160,323

(22) PCT Filed: Jan. 10, 2007

(86) PCT No.: PCT/US2007/060316
§ 371 (c)(1),
(2), (4) Date: Jul. 9, 2008

(87) PCT Pub. No.: WO2007/082226
PCT Pub. Date: Jul. 19, 2007

(65) Prior Publication Data
US 2009/0012478 A1 Jan. 8, 2009

(30) Foreign Application Priority Data

Jan. 10, 2006 (GB) .................................. 0600351.1

(51) Int. Cl.
*A61M 5/00* (2006.01)
*A61M 5/32* (2006.01)
*A61M 5/31* (2006.01)

(52) U.S. Cl.
CPC ............... *A61M 5/002* (2013.01); *A61M 5/326* (2013.01); *A61M 5/3213* (2013.01); *A61M 2005/312* (2013.01); *A61M 2005/3247* (2013.01); *A61M 2005/3268* (2013.01)

(58) Field of Classification Search
CPC ............ A61M 5/3202; A61M 5/5086; A61M 5/3134; A61M 25/0631; A61M 2005/3247; A61M 5/002; A61M 5/326; A61M 5/3213; A61M 2005/312; A61M 2005/3268
USPC .................. 604/110, 111, 171, 192–199
See application file for complete search history.

(56) References Cited

U.S. PATENT DOCUMENTS 5,549,568 A * 8/1996 Shields ...................... 604/192
6,196,998 B1 * 3/2001 Jansen et al. ............... 604/111
(Continued)

FOREIGN PATENT DOCUMENTS

EP 1466638 A2 10/2004
EP 1535640 A1 6/2005
(Continued)

OTHER PUBLICATIONS

Office Action Issued Jul. 14, 2010 in CN Application No. 200780002174.X.
(Continued)

*Primary Examiner* — Emily Schmidt
*Assistant Examiner* — Lauren M Peng
(74) *Attorney, Agent, or Firm* — Panitch Schwarze Belisario & Nadel LLP

(57) ABSTRACT

A safety needle accessory is provided for the prevention of needle stick injuries. The safety needle accessory includes a hollow needle, a hub surrounding a base of the hollow needle, a sleeve surrounding the hub, and a elastically deformable member. The sleeve is slidable to a first, a second and a third position in which the sleeve fully or partially covers the needle. In addition, the safety needle accessory includes a pack having a removable cap. The cap is removable from the pack while a remainder of the pack remains mounted over the needle, hub and sleeve. The cap is removed from the pack at a position such that removal of the cap exposes a sharp end of the needle, but not the sleeve, when the sleeve is in the intermediate position.

21 Claims, 3 Drawing Sheets

(56) References Cited

U.S. PATENT DOCUMENTS

| | | |
|---|---|---|
| 2005/0027259 A1 | 2/2005 | Vetter et al. |
| 2005/0148932 A1* | 7/2005 | Rimlinger et al. ............ 604/110 |
| 2005/0203459 A1* | 9/2005 | Alchas .......................... 604/117 |
| 2005/0277893 A1* | 12/2005 | Liversidge ................... 604/198 |

FOREIGN PATENT DOCUMENTS

| | | | |
|---|---|---|---|
| FR | 2 736 553 A1 | 1/1997 | |
| FR | 2 741 268 A1 | 5/1997 | |
| GB | WO 2004071560 A1 * | 8/2004 | ........... A61M 5/326 |
| WO | 8802638 A1 | 4/1988 | |
| WO | 2004/071560 A1 | 8/2004 | |
| WO | 2004103431 A2 | 12/2004 | |
| WO | 2006/082350 A1 | 8/2006 | |
| WO | 2006/090118 A1 | 8/2006 | |

OTHER PUBLICATIONS

Office Action issued Dec. 12, 2011 in CN Application No. 200780002174.X.

Office Action issued Jan. 26, 2012 in EP Application No. 07710031.1.

Office Action issued Aug. 27, 2014 in EP Application No. 07 710 031.1.

* cited by examiner

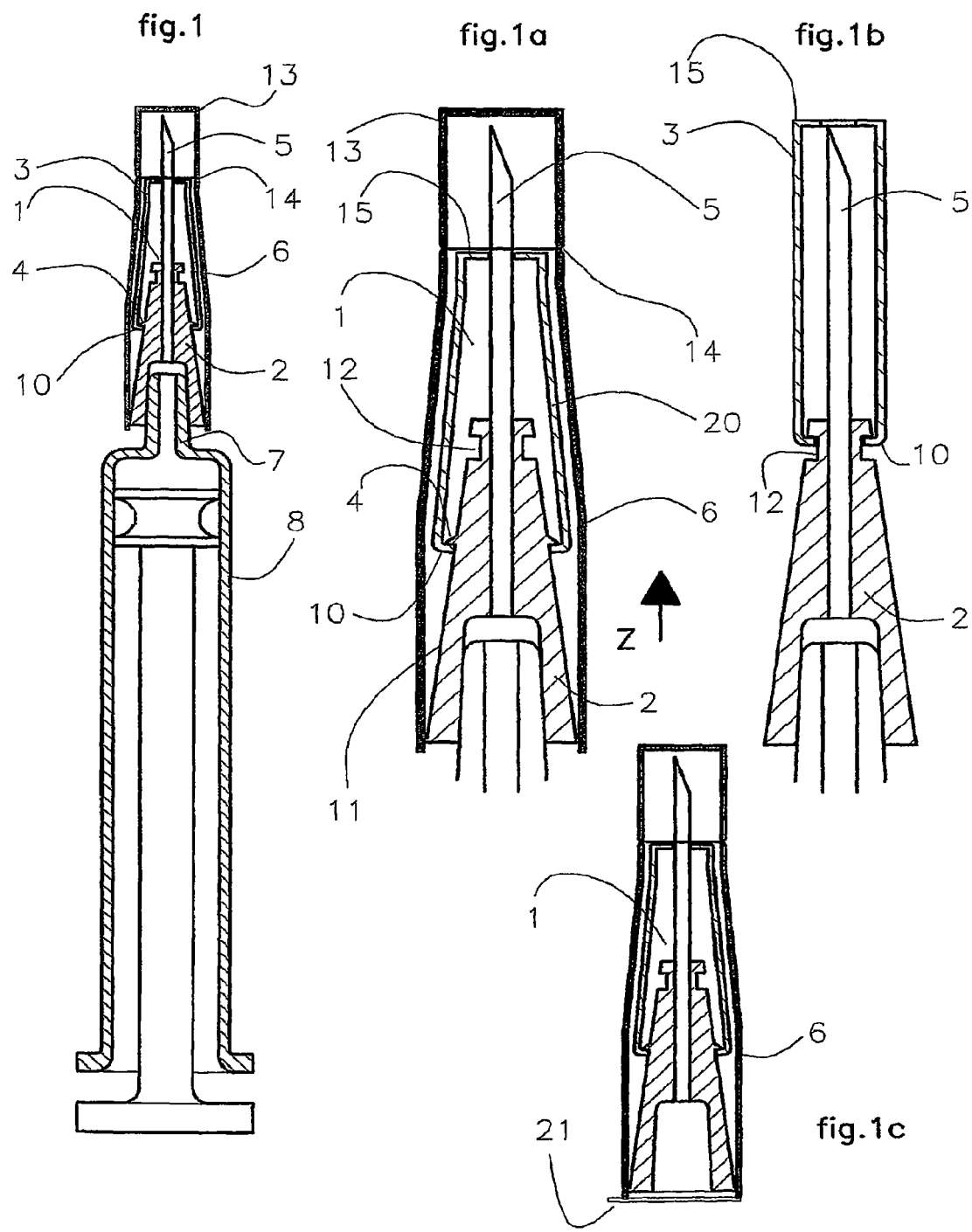

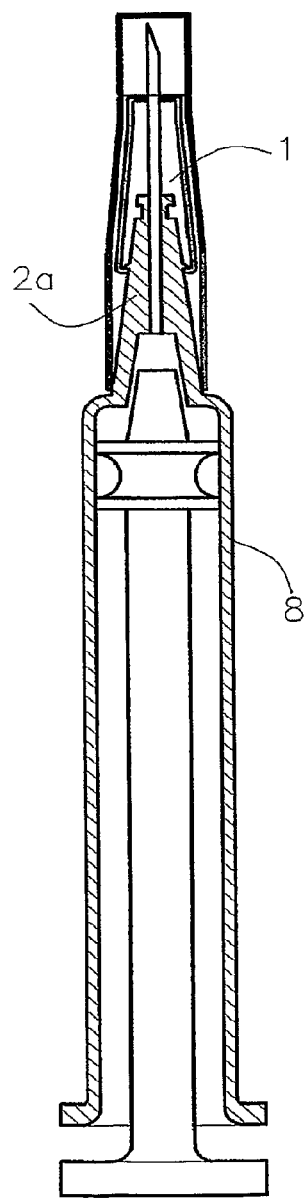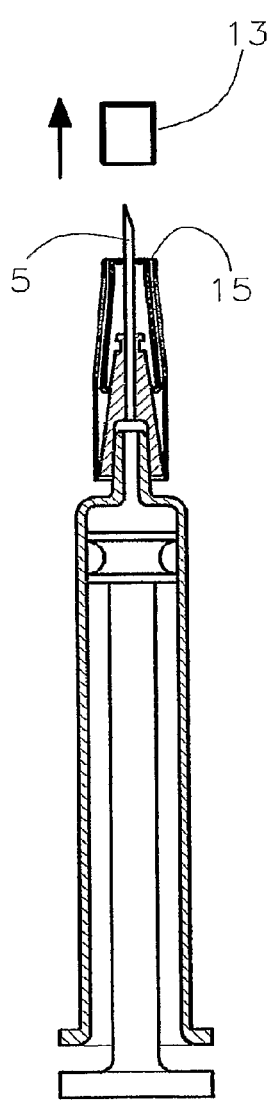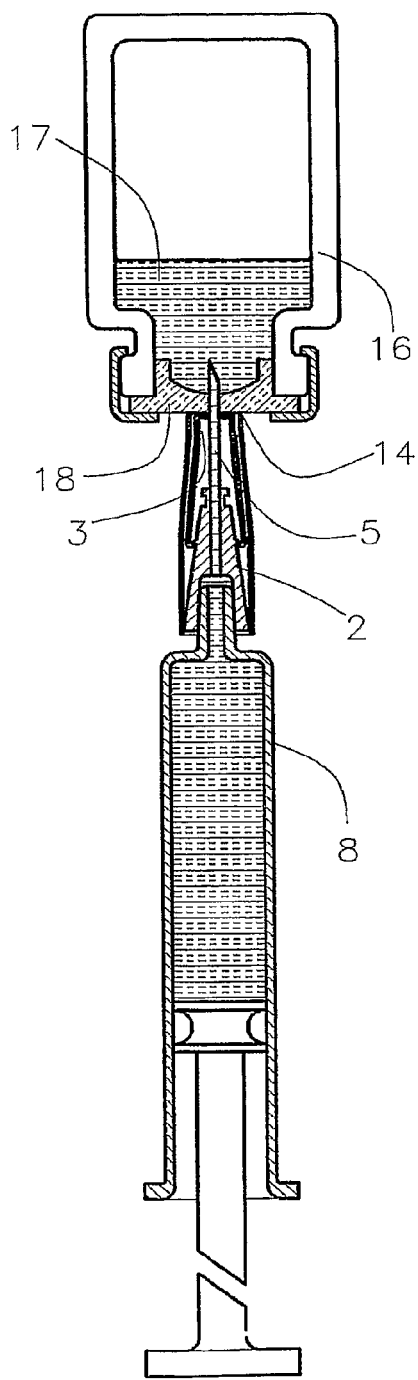

SAFETY NEEDLE

CROSS-REFERENCE TO RELATED APPLICATIONS

This application is a Section 371 of International Application No. PCT/US2007/060316, filed Jan. 10, 2007, which was published in the English language on Jul. 19, 2007, under International Publication No. WO 2007/082226 A1 and the disclosure of which is incorporated herein by reference.

BACKGROUND OF THE INVENTION

This invention relates to a safety needle accessory and in particular to safety needle accessory incorporating a protective pack. Safe hypodermic needles reduce the risk of needle stick injuries, and are increasingly specified in many healthcare areas as a means of reducing cross-infection with serious diseases. Generally, these devices employ a sliding sleeve which is biased towards the sharp tip of the needle, so that after use, the end of the sleeve prevents easy access to the needle tip. The sleeve may be operated manually, so-called "active" safety needles, or automatically, known as "passive" safety needles. Passive needles are preferred because the needle is covered during the whole of the injection procedure, and as the needle is withdrawn, the sleeve slides towards and then covers the needle tip. The whole procedure is automatic and independent of the user. In most cases, the sleeve locks in the safe position to prevent inadvertent contact with the needle, and to prevent re-use.

Most safety needles are sold separately as accessories, whereby the user puts the device onto a pre-filled syringe. Good practice requires that the syringe is filled with a different needle to the needle that is to be inserted in the patient. The reasons are that the rubber seal on the vial from which the medicament is withdrawn may have surface contamination, or a piece of the rubber seal may partially block the needle ("coring"), and the small needles used for many injections have a low flow rate, which, during filling, can cause foaming of the medicament. Thus, a large needle might be used to fill the syringe, which is then removed and replaced by the small injection needle. However, even in the most assiduous of healthcare practices, frequently the same needle is used to fill the syringe and to inject the patient. This is probably because despite the theoretical risks, in practice, many billions of injections have been given without problems. It is often preferred that the needle tip is exposed for 4-5 mm prior to use, to facilitate aspiration of air trapped in the syringe, and to enable accurate placement on the injection site. Apart from the risk of an unpleasant scratch from the exposed needle tip, there is practically no risk of cross-infection, since the needle has not been used to inject a patient.

A problem arises with safety needles however, particularly with the preferred passive type. Usually with the passive types, the initial movement of the sleeve towards the syringe when injecting the patient enables the safety mechanism. Clearly, if such a needle were used to fill a syringe from a vial, the safety mechanism would operate and prevent the needle being used to inject a patient. The only solution would be to replace the used needle with a new one—which could be considered too expensive and time consuming.

BRIEF SUMMARY OF THE INVENTION

Accordingly, the present invention provides a safety needle accessory comprising a hollow needle having a base end and a sharp end, a hub surrounding the base end of the needle and having a connector for connection to an injection device, a sleeve surrounding the hub and slidable relative to the hub in an axial direction, an elastically deformable member, and a pack having a closed end covering the sharp end of the needle and an open end exposing the connector of the hub and which is releasably mounted over the needle, hub and sleeve, and wherein the sleeve is slidable in a first axial direction from a first position in which the needle is fully or partially covered by the sleeve to a second position in which the needle is exposed, via an intermediate position between the first and second positions in which the sharp end of the needle projects from the sleeve, and in a second axial direction from the second position to a third position in which the needle is fully covered by the sleeve, wherein the deformable member is deformed by the sleeve sliding from the first to the second position and the force for sliding from the second to the third position is provided by the stored elastic energy in the deformable member, and wherein the closed end of the pack has a removable cap at a position on the pack such that removal of the cap exposes the sharp end of the needle but not the sleeve when the sleeve is in the intermediate position.

This safety needle accessory protects the user from needle stick injuries while still allowing the sharp end of the needle to be exposed for filing the syringe with the injectate from a vial or other appropriate container prior to performing the injection. The present invention also provides a device comprising the accessory described herein and an injection device (e.g. a syringe), as well as a method for preparing an injection comprising the steps of providing the device, removing the cap, and filling the injection device with an injectate from a suitable container. The present invention further provides a method for injecting a patient using the device as defined above.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a general assembly of a safety needle assembled to a syringe, shown in section taken on the longitudinal axis, FIG. 1a is an enlarged view of the safety needle and protective pack, and a simplified view of a safety needle, FIG. 1b shows only the safety needle in its safe position after use, and FIG. 1c shows the pack as supplied with a removable seal covering the syringe connecting end of the safety needle;

FIG. 2 shows a safety needle with integral syringe, fitted with the device of the invention;

FIG. 3 shows the removable needle-protecting cap removed;

FIG. 4 shows the syringe and safety needle assembly being used to withdraw liquid medicament from a typical vial;

DETAILED DESCRIPTION OF THE INVENTION

Figure 5:
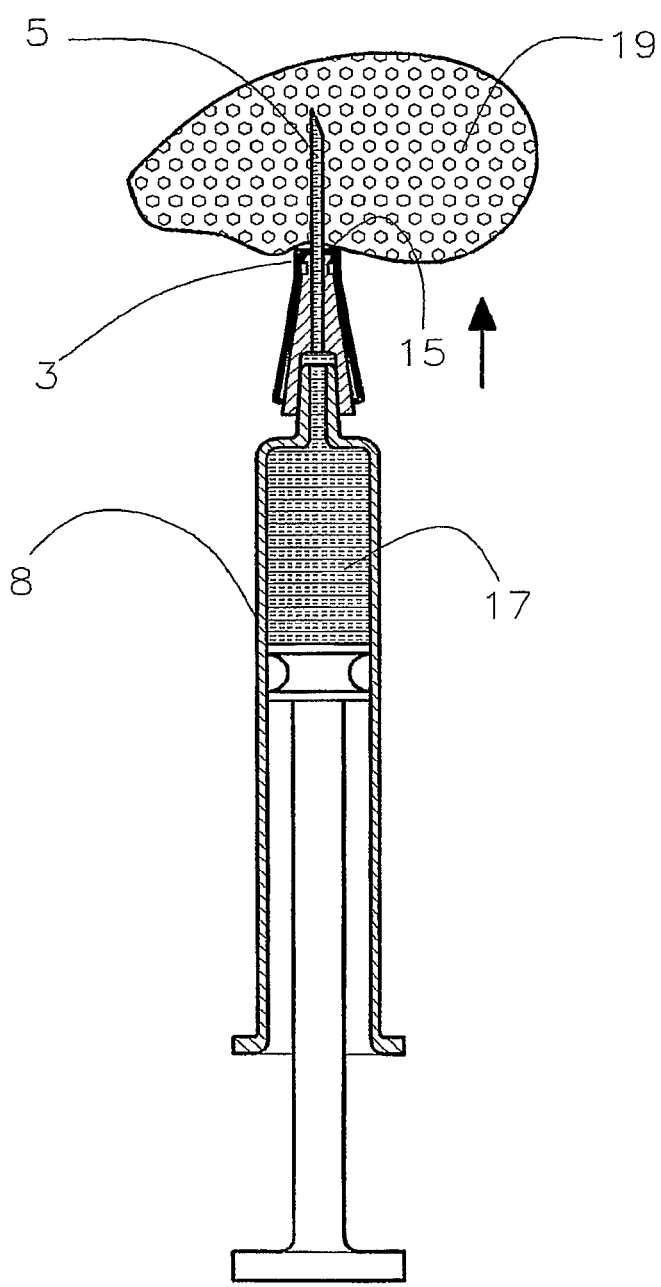
FIG. 5 is a view of the safety needle inserted in tissue.

In the drawings, like parts are given the same reference numerals.

The present invention provides a means of overcoming the problem of filling a syringe when using some types of passive safety needle. The following descriptions are based on the use of the safety needle disclosed in WO 2004/071560 but are applicable to many other safety needles which use a biased sliding sleeve that covers the needle after use and locks.

The present invention makes use of the packaging to provide blocking means to prevent the sleeve moving during filling. The packing is removed after filling, and the safety needle is used in the normal way. It is common to supply needles in a stiff tubular pack, which is used to hold the needle safely when fitting it to the syringe. The pack is then removed by pulling it off in an axial direction. Thus the present invention does not add to the cost of the needle, but does provide additional benefit.

The needle packed within a stiff protective pack, the pack having a snap-off cap which is removed to expose the needle tip, and the other end has a peel-off seal or other removable seal, which is removed to enable the needle to be fitted to a syringe. Alternatively the cap is retained on the pack by a tear-off band or the cap is a push-on separate part, or a plug.

In a preferred embodiment, the safety needle is integral with a syringe, and fitted with a stiff protective sleeve. The sleeve has a removable cap or plug as described above, and the remainder of the pack is pulled off after the syringe has been filled.

FIG. 1 is a general assembly of a syringe 8 with a safety needle accessory 1 incorporating a protective pack 6. The safety needle accessory 1 is shown comprising a conical hub 2, having connecting means to fit the syringe outlet 7, which may be a Luer slip, Luer lock or other types of outlet. The hub 2 holds a needle 5, and has a sliding sleeve 3. The following brief description of the mode of action is based on the device disclosed in WO 2004/071560, but apart from the biasing effect of the sleeve in that invention, the effect of the device is similar to several other prior art safety needles. Referring to FIG. 1*a*, and ignoring the pack 6 for the moment, sliding sleeve 3 has resilient cantilever arms 20 which are displaceable radially. The radially displaceable cantilever arms 20 exemplify the deformable member which in this case is integral with the sleeve 3. The arms 20 terminate with pawls 10 which rest on the surface 11 of the hub 2, and may slide longitudinally on the surface 11. The accessory 1 may be supplied with the sleeve 3 fully or partially surrounding the sharp end of the needle 5 (the first position). Alternatively, as shown in FIG. 1*a*, the sleeve 3 may be partially retracted so as to expose the sharp end of the needle 5 (the intermediate position). However, this partial retraction intentionally does not provide sufficient depth to insert the needle 5 into the patient and is not sufficient to activate the safety mechanism.

As the sleeve 3 is caused to move towards the hub 2 (the first axial direction), the resilient cantilever arms 20 react against the conical surface 11 to cause a biasing force in the direction of the arrow Z (the second axial direction). The sleeve 3 is temporarily prevented from sliding down the hub 2 by detents 4 acting against the pawls 10.

Figure 6:
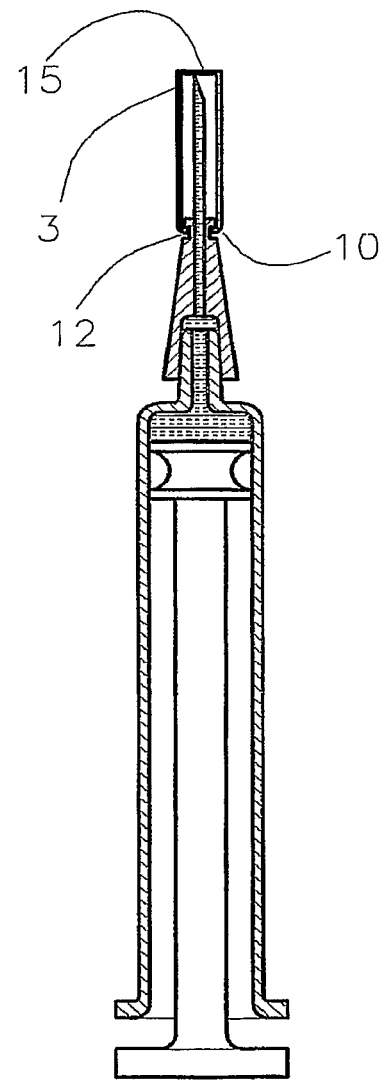
FIG. 6 shows the position assumed by the safety sleeve after the injection.

In use the needle 5 is pushed into the patient's tissue 19, (as shown in FIG. 5) in the direction of the arrow, and when the face 15 of sleeve 3 contacts the patient's skin, sleeve 3 is pushed towards the syringe. This causes the pawls 10 of sleeve 3 to disengage from the detents 4 and the sleeve 3 continues to slide along the hub 2 towards the syringe. At this stage the sleeve is essentially fully retracted (the second position). When the needle 5 is withdrawn from the tissue 19, the sleeve 3 slides back down the conical hub 2 until the pawls 10 drop into the annular groove 12 of the hub 2. This locks the sleeve 3, preventing further longitudinal movement relative to the hub 2, and the end 15 of the sleeve 3 restricts exposure to the tip of the needle 5 and reduces the risk of needle-stick injury. This final (third) position of the sleeve 3 is shown in FIGS. 1*b* and 6.

It is a usual feature of safety needles to have a short initial movement of the protective sleeve in order to disengage a temporary detent position and "switch" the pawls or similar detent means onto a track which is connected to a final locking detent. Thus, after the initial movement, when the needle is withdrawn from the patient, the sleeve is biased to return to a safe locked position and the accessory further comprises a locking mechanism which locks the sleeve in this third position. The locking mechanism preferably comprises a latching pawl on the inside surface of the sleeve and a shoulder on the outside surface of the hub, or a latching pawl on the hub and a track on the sleeve.

It is a feature of the present invention to provide a pack for the safety needle which temporarily blocks the initial movement in the first axial direction. Referring to FIG. 1*a*, the protective pack 6 has a cap 13, which is removably (in this case frangibly) connected to the main part of the pack at connection 14. Preferably, the cap 13 is twisted relative to the main pack, which shears the frangible connection 14 and allows the cap 13 to be removed. In another embodiment, the frangible connection 14 is replaced by a tear-off band. This is a well-known device and is therefore not illustrated. Again, an alternative is to use a pull-off cap, or a plug, which is also not shown.

When the cap 13 is removed, a short part of the needle 5 is exposed, as shown in FIG. 3. In FIG. 4 it may be seen that the length of the exposed part should be sufficient to allow the needle 5 to be pushed through the seal 18 of a vial 16, and make fluid connection with the contents 17 of the vial. Without the present invention, this action would merely push the sleeve 3 along the hub 2 and activate the safety device. Then, if the needle 5 were to be withdrawn from the seal 18, the sleeve 3 would return to a locked position and render the safety needle inoperable. To prevent this from occurring, the position of the frangible connection 14 of the pack 6 is such that the sliding sleeve 3 is not exposed and hence cannot touch the seal 18 of the vial 16, so that during filling, the sliding sleeve 3 cannot be moved. After filling and removing the assembly from the vial, the remainder of the pack 6 is pulled off the safety needle and the injection is given.

For cost-effectiveness, the removable cap 13 may be moulded integrally with the main body of the pack 6, and include either a tear-off band or a frangible joint. If a separate cap or plug is used, then the position of the end of the pack 6 after removing the cap or plug must be the same as that for the frangible connection 14. If the safety needle is to be supplied in the pack without any additional protection, then the cap 13 would normally be sealingly attached to the main body of the pack 6, to prevent contamination of the needle, and a removable seal 21 would be applied to the syringe connection end of the pack, as shown in FIG. 1*c*.

The pack 6 is releasably mounted on the needle, sleeve and hub (preferably just on the needle hub), that is the pack 6 is held in place, for example by friction, but may be removed by the user. To facilitate the releasable mounting the pack and accessory may have engageable portions which may simply be the surfaces of the pack and accessory. These surfaces may be textured or have projections. The pack 6 preferably substantially tubular and also preferably made from a deep-drawn vacuum-formed plastics material. The safety needle may be further retained inside the pack 6 by a releasable (peel-off) membrane 21, which is preferably gas permeable. The membrane 21 is bonded to a flange, and may be made from a porous material such as TYVEK® brand spunbonded olefin i.e., a spun-bonded high-density polyethylene available from DuPont and which is used extensively in pharmaceutical packaging to permit a sterilizing gas, such as ethylene oxide, to penetrate the pack whilst preventing ingress of bacteria during storage. Other peelable materials may be used according to the sterilization process used. The membrane 21 may have a tag to assist removal.

A more cost-effective embodiment is that shown in FIG. 2. In this case, the safety needle accessory 1 operates similarly to that already described, but the hub 2a is made integrally with the body of the syringe 8. Preferably in this embodiment, the pack 6 seals against the hub 2a to prevent contamination of the safety needle.

There are a number of injection devices other than syringes, such as reconstitution devices for lyophilized drugs, where it is desirable to have an automatic safety feature to protect the user from sharps injuries, and yet have an intermediate stage where access is available to the sharp part. The present invention is applicable to many of those devices, and this invention disclosure is intended to cover those devices.

In FIG. 1a, the accessory 1 is shown with the sleeve 3 partially retracted in the intermediate position so as to expose the sharp end of the needle 5. This is a preferred since the user simply has to remove the cap to fill the syringe. That is, it is preferred for the first position to be axially the same position as the intermediate position. In this intermediate position, the pack is not in any substantial contact with the sleeve. Thus, the pack does not exert sufficient force on the sleeve to cause the sleeve to move in the first axial direction. However, the accessory may also be provided with sleeve fully or partially surrounding the sharp end of the needle. The pack may then be used to "prime" the sleeve. In this embodiment, the pack abuts against the sleeve and the user causes the sleeve to move from the first to the intermediate position by moving the pack in the first axial direction. This so-called "active-packaging" concept is more fully described in EP 1 535640. Once the accessory has been moved to the intermediate position, the cap may be removed as described hereinabove.

The elastically deformable member may be a separate component or may formed integrally with the sleeve or the hub, or by a combination of the two. Preferably the accessory is provided such that, prior to use, the deformable member is not under any substantial load. An example of a separate deformable member is a helical spring. Compression of the helical spring as the sleeve moves in the first axial direction provides the restoring force which causes the sleeve to move in the second axial direction. Such safety needles are exemplified in U.S. Pat. No. 4,911,693, U.S. Pat. No. 4,813,940 and U.S. Pat. No. 5,104,384.

In addition, or preferably as an alternative, the elastically deformable member is formed integrally with the sleeve or the hub. For example, the sleeve has a radially elastically deformable portion and the hub has radially converging or diverging portion, and sliding the sleeve in the first axial direction causes elastic radial deformation of the deformable portion of the sleeve by sliding of the radially elastically deformable portion of the sleeve directly on the converging or diverging portion of the hub.

Alternatively, the sleeve has a radially converging interior portion, and the hub has a radially elastically deformable portion, and sliding the sleeve in the first axial direction causes elastic radial deformation of the deformable portion of the hub by sliding of the radially elastically deformable portion of the hub directly on the converging interior portion of the sleeve.

The present invention has been described hereinabove with reference to cantilever arms incorporated into the sleeve. As an alternative to cantilever arms, the sleeve itself may have elastic properties such that, in use, as the needle is inserted into a patient, the resultant force is generated within the slidable sleeve. By elastic properties the applicant means that the resultant force is generated within a radially continuous slidable sleeve, i.e. a sleeve without cantilever arms. The elastic properties may be achieved by using an elastic material, such as an elastomeric polymer. Alternatively, the receiving end of the slidable sleeve may be concertinaed, with the ridges, of course, running parallel to the hollow needle. The elastic properties could also be generated using a circumambient spring attached to the slidable sleeve.

It is preferable that the coefficient of friction between the slidable sleeve 3 and the needle hub 2 is low, so that the resultant biasing force to return the slidable sleeve is not compromised by "stiction", or so high that the force required on the patient's skin to deflect the slidable sleeve 3 is excessive. This may be achieved by careful selection of materials. Such materials are known in the art, for example, the needle hub could be made from a high-density polyethylene or similar drug-compatible plastics material, and the slidable sleeve from an inexpensive plastics material such as polycarbonate, polystyrene, polyester or PVC. A more expensive, highly creep-resistant plastics material, for example polyphenylene sulfone, could also be used. As an alternative, the slidable sleeve, or just the at least one cantilever arm, may be made from metal, preferably stainless steel. The metal would be fabricated sufficiently thinly to provide the required elastic properties. If necessary, a lubricant may be used, or a lubricant may be incorporated with the polymers. Generally the materials should be suitable for sterilization by gamma radiation, but it is possible to select materials compatible with sterilization by steam or other gas such as ethylene oxide.

Other modifications of the present invention falling within the scope of the claims will be apparent to those skilled in the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A safety needle accessory comprising:
   a hollow needle having a base end and a sharp end,
   a hub, surrounding the base end of the needle, having a connector for connection to an injection device,
   a sleeve, surrounding the hub, slidable relative to the hub in an axial direction, the sleeve including a face for skin contact,
   an elastically deformable member, and
   a pack, comprising a cap, a main part, and a frangible connection that frangibly connects the cap and the main part, wherein the cap covers the sharp end of the needle and the main part includes an open end exposing the connector of the hub, the pack being releasably mounted over the needle, the hub and the sleeve, and completely removable from the needle, the hub and the sleeve,
   wherein the sleeve is slidable in a first axial direction from a first position in which the needle is fully or partially covered by the sleeve to a second position in which the needle is exposed, via an intermediate position between the first and second positions in which the sharp end of the needle projects from the sleeve, and in a second axial direction from the second position to a third position in which the needle is fully covered by the sleeve, wherein the deformable member is deformed by the sleeve sliding from the first position to the second position and the force for sliding the sleeve from the second to the third position is provided by elastic energy stored in the deformable member, and wherein, when the sleeve is in the intermediate position, the frangible connection is positioned such that when the cap is removed from the main part, the sharp end of the needle is exposed but the sleeve is not exposed, and, therefore, the sleeve is shielded by the main part from sliding movement upon contact of the sharp end of the needle with the skin, and when the pack is removed from the needle, the hub and the sleeve, the sleeve is slidable between the first, intermediate, second and third positions thereof.

2. A safety needle accessory as claimed in claim 1, wherein the pack is mounted on the needle hub.

3. A safety needle accessory as claimed in claim 2, wherein the pack is not in any substantial contact with the sleeve when the sleeve is in the intermediate position.

4. A safety needle accessory as claimed in claim 1, wherein the pack is substantially tubular.

5. A safety needle accessory as claimed in claim 1, wherein the open portion of the pack is covered by a releasable membrane.

6. A safety needle accessory as claimed in claim 1, wherein the pack is made from a vacuum-formed plastics material.

7. A safety needle accessory as claimed in claim 1, wherein the elastically deformable member is formed integrally with the sleeve or the hub.

8. A safety needle accessory as claimed in claim 7, wherein the sleeve has a radially elastically deformable portion and the hub has a radially converging or diverging portion, and sliding of the sleeve in the first axial direction causes elastic radial deformation of the deformable portion of the sleeve by sliding of the radially elastically deformable portion of the sleeve directly on the converging or diverging portion of the hub.

9. A safety needle accessory as claimed in claim 7, wherein the sleeve has a radially converging interior portion, and the hub has a radially, elastically deformable portion, and sliding of the sleeve in the first axial direction causes elastic radial deformation of the deformable portion of the hub by sliding of the radially elastically deformable portion of the hub directly on the converging interior portion of the sleeve.

10. A safety needle accessory as claimed in claim 7, wherein the deformable portion of the sleeve or hub comprises at least one cantilever arm which bears resiliently on a diverging or converging portion of the hub or sleeve, respectively.

11. A safety needle accessory as claimed in claim wherein the deformable member is a helical spring.

12. A safety needle accessory as claimed in claim 1, wherein the accessory further comprises a locking mechanism which locks the sleeve in the third position.

13. A safety needle accessory as claimed in claim 12, wherein the locking mechanism comprises a latching pawl on the inside surface of the sleeve and a shoulder on the outside surface of the hub, or a latching pawl on the hub and a track on the sleeve.

14. A safety needle accessory as claimed in claim 1, wherein the safety needle accessory is constructed from materials capable of being sterilized with gamma irradiation, steam and/or ethylene oxide.

15. A safety needle accessory as claimed in claim 1, wherein the elastically deformable member, prior to use, is not under any substantial load.

16. A safety needle accessory as claimed in claim 1, wherein the first position is the same axially as the intermediate position.

17. A device comprising the accessory as claimed in claim and an injection device.

18. An injection device as claimed in claim 17, wherein the needle and the hub are integral with the injection device.

19. An injection device as claimed in claim 17, wherein the injection device is a syringe.

20. A method for preparing an injection comprising the steps of:
providing a device as claimed in claim 17,
removing the cap,
filling the injection device with an injectate from a suitable container, and
removing the remainder of the pack from the safety needle accessory.

21. A safety needle accessory comprising:
a hollow needle having a base end and a sharp end,
a hub, surrounding the base end of the needle, having a connector for connection to an injection device,
a sleeve, surrounding the hub, slidable relative to the hub in an axial direction, the sleeve including a face for skin contact,
an elastically deformable member, and
a pack, comprising a cap, a main part, and a frangible connection, the frangible connection frangibly connecting the cap and the main part, wherein the cap covers the sharp end of the needle and the main part includes an open end exposing the connector of the hub, the pack being releasably mounted over the needle, the hub and the sleeve, wherein the sleeve is slidable in a first axial direction from a first position in which the needle is fully or partially covered by the sleeve to a second position in which the needle is exposed, via an intermediate position between the first and second positions in which the sharp end of the needle projects from the sleeve, and in a second axial direction from the second position to a third position in which the needle is fully covered by the sleeve, wherein the deformable member is deformed by the sleeve sliding from the first to the second position and the force for sliding the sleeve from the second to the third position is provided by elastic energy stored in the deformable member, and wherein, when the sleeve is in the intermediate position, the frangible connection is positioned such that when the cap is removed from the main part, the sharp end of the needle is exposed but the sleeve is not exposed, and, therefore, the sleeve is shielded by the main part from sliding movement upon contact of the sharp end of the needle with the skin, and when the pack is removed from the needle, the hub and the sleeve, the sleeve is slidable between the first, intermediate, second and third positions thereof.

* * * * *